United States Patent
Ward et al.

(10) Patent No.: US 10,946,210 B2
(45) Date of Patent: Mar. 16, 2021

(54) CELLULITE AND FAT REDUCING DEVICE AND METHOD UTILIZING OPTICAL EMITTERS

(71) Applicants: Terry Ward, Cocoa Beach, FL (US); Carolyn Ward, Cocoa Beach, FL (US)

(72) Inventors: Terry Ward, Cocoa Beach, FL (US); Carolyn Ward, Cocoa Beach, FL (US)

(73) Assignee: Blue Water Innovations, LLC, Charlestown (KN)

( * ) Notice: Subject to any disclaimer, the term of this patent is extended or adjusted under 35 U.S.C. 154(b) by 93 days.

(21) Appl. No.: 14/532,583

(22) Filed: Nov. 4, 2014

(65) Prior Publication Data

US 2015/0127075 A1    May 7, 2015

Related U.S. Application Data

(60) Provisional application No. 61/900,809, filed on Nov. 6, 2013.

(51) Int. Cl.
*A61N 5/06*    (2006.01)

(52) U.S. Cl.
CPC .... *A61N 5/0616* (2013.01); *A61N 2005/0626* (2013.01); *A61N 2005/0642* (2013.01); *A61N 2005/0652* (2013.01); *A61N 2005/0662* (2013.01)

(58) Field of Classification Search
CPC .......... A61N 5/0616; A61N 2005/0645; A61N 2005/0662; A61N 2005/0663
See application file for complete search history.

(56) References Cited

U.S. PATENT DOCUMENTS

| | | | |
|---|---|---|---|
| 5,143,063 A | 9/1992 | Felner | |
| 5,507,790 A | 4/1996 | Weiss | |
| 6,602,275 B1 * | 8/2003 | Sullivan | A61N 5/0616 606/10 |
| 6,645,162 B2 | 11/2003 | Friedman et al. | |
| 7,351,252 B2 | 4/2008 | Altshuler et al. | |
| 7,993,382 B2 | 8/2011 | Shanks et al. | |
| 8,366,756 B2 | 2/2013 | Tucek et al. | |
| 8,614,632 B1 * | 12/2013 | Wells | H05B 37/029 340/331 |
| 8,813,756 B1 * | 8/2014 | Shanks | A61N 5/0613 128/898 |

(Continued)

OTHER PUBLICATIONS

Jackson et al, A double-blind, placebo-controlled randomized trial evaluating the ability of low-level laser therapy to improve the appearance of cellulite, Lasers Surg Med, Mar. 2013; 45(3):141-7.*

(Continued)

*Primary Examiner* — Niketa I Patel
*Assistant Examiner* — Nathan A Baldwin
(74) *Attorney, Agent, or Firm* — Jason T. Daniel, Esq.; Daniel Law Offices, P.A.

(57) ABSTRACT

A cellulite and fat reducing device and method utilizing optical emitters includes an array housing a plurality of optical emitters which are positioned to produce an optical output directed to a recipient, and a controller for instructing an operation of the array. The optical output being generated by a plurality of LED's cumulatively producing green light at approximately 529.6 nm, and at approximately 48,860 Lux, measurable at the array.

8 Claims, 9 Drawing Sheets

(56) References Cited

U.S. PATENT DOCUMENTS

| | | | |
|---|---|---|---|
| 2005/0197681 A1* | 9/2005 | Barolet | A61B 18/203 607/86 |
| 2006/0064144 A1* | 3/2006 | Chen | A61N 5/0618 607/90 |
| 2007/0038206 A1* | 2/2007 | Altshuler | A46B 15/0036 606/20 |
| 2007/0197884 A1 | 8/2007 | Bornstein | |
| 2008/0091250 A1* | 4/2008 | Powell | A61M 21/00 607/90 |
| 2009/0075557 A1* | 3/2009 | Arriola | A63H 17/268 446/438 |
| 2012/0022618 A1* | 1/2012 | Lum | A61N 5/0616 607/90 |
| 2013/0190844 A1* | 7/2013 | Tu | A61N 5/0616 607/90 |
| 2014/0375434 A1* | 12/2014 | Puljan | F21V 33/004 340/12.5 |

OTHER PUBLICATIONS

"Colour ." A Dictionary of Physics, Oxford University Press, 2009. (Year: 2009).*
U.S. Appl. No. 13/784,166, filed after the present application, by Heidi Araya Plaintiff in the above noted case.

* cited by examiner

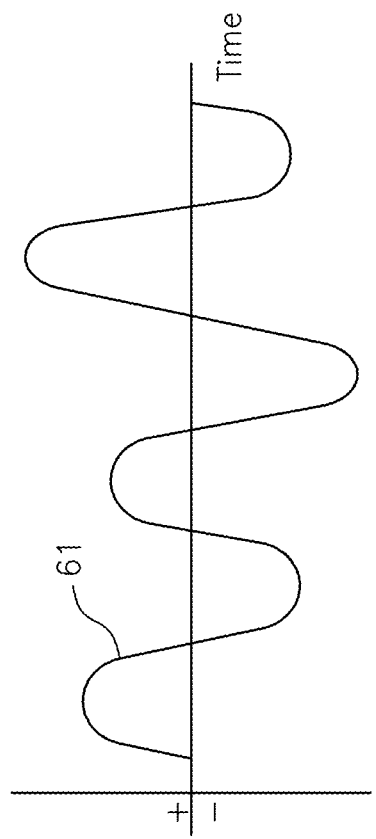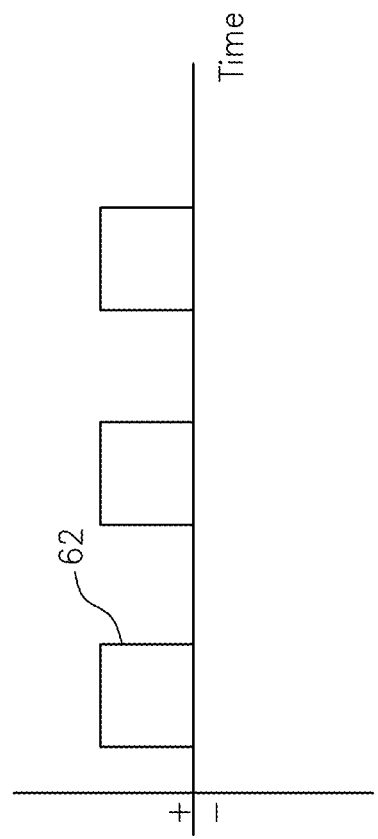
FIG. 6a
FIG. 6b

CELLULITE AND FAT REDUCING DEVICE AND METHOD UTILIZING OPTICAL EMITTERS

CROSS-REFERENCE TO RELATED APPLICATIONS

This application is a continuation-in-part to, and claims the benefit of U.S. Application Ser. No. 61/900,809 filed on 6 Nov. 2013, the contents of which are incorporated herein by reference.

TECHNICAL FIELD

The present invention relates generally to the field of body shaping, and more particularly, to a device and method for reducing the appearance of cellulite utilizing optical emitters.

BACKGROUND

The statements in this section merely provide background information related to the present disclosure and may not constitute prior art.

Cellulite is a condition of the body wherein persistent subcutaneous fat accumulates at specific locations to cause a noticeable dimpling of the skin. Background FIG. 1, illustrates a side by side comparison of the fat cell structure within women and men. As shown, owing to the differences in the structure, cellulite is most commonly found in women, and typically forms about the thighs, hips, stomach and upper arms.

Unlike other forms of fat which can be reduced through diet and exercise, cellulite and the resulting "cottage cheese" appearance of the skin do not react to these traditional methods. As a result, cellulite can be found in individuals of all body types having body mass indexes ranging from "normal" to "overweight" and "obese."

As a result of the above, a number of approaches have been proposed to temporarily reduce the appearance of cellulite. For example, one approach may involve a user using creams such as those containing Caffeine or Aminophylline to temporarily reduce the appearance of cellulite. However, such creams are messy, with no immediate results (in fact, most see no reduction in the appearance of cellulite for 4 to 6 weeks with daily use), maintenance is difficult to achieve and even harder to maintain, and even when results are good, and the recurring costs can be quite expensive. Furthermore, many of the lotions and creams that are applied topically can require multiple applications per week, can require the use of drugs or chemicals, can be irritating to the skin and must be used consistently over time to achieve then maintain desirable results.

In a different field of study, recent advancements in light emitting devices have seen the introduction of laser and LED systems which can target more traditional fat cells, such as those described above that are affected by diet and exercise. One such example is described in U.S. patent application Ser. No. 13/782,377 entitled fat reducing device and method utilizing optical emitters, the contents of which are incorporated herein by reference.

Accordingly, it would be beneficial to provide a device and method which can effectively reduce cellulite and/or the appearance of cellulite utilizing a plurality of non-invasive optical emitters, and which does not suffer from the above noted drawbacks.

SUMMARY OF THE INVENTION

The present invention is directed to a cellulite and fat reducing device and method utilizing optical emitters. One embodiment of the present invention can include an array housing a plurality of optical emitters which can be positioned to produce an optical output directed to a recipient, and a controller for instructing an operation of the array. The optical output can be generated by a plurality of LED's cumulatively producing green light at approximately 529.6 nm, and at approximately 48,860 Lux, measurable at the array.

Another embodiment of the present invention can include components for modulating the power delivered to the array based on a reference waveform created internally or via an external device.

Yet another embodiment of the present invention can include a method of reducing the appearance of cellulite using the optical emitting device. The method including delivering green light at approximately 383 Lux at a wavelength of approximately 529.6 nm for between 15 and 25 minutes, resulting in a total delivery of 8.8 Joules to the subcutaneous adipocytes of the target area of the recipient.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

FIGS. 6a and 6b are diagrams of the modulation input signal and the rectified input signal, respectively, in the controller of FIG. 4a.

DETAILED DESCRIPTION OF THE INVENTION

Figure 1:
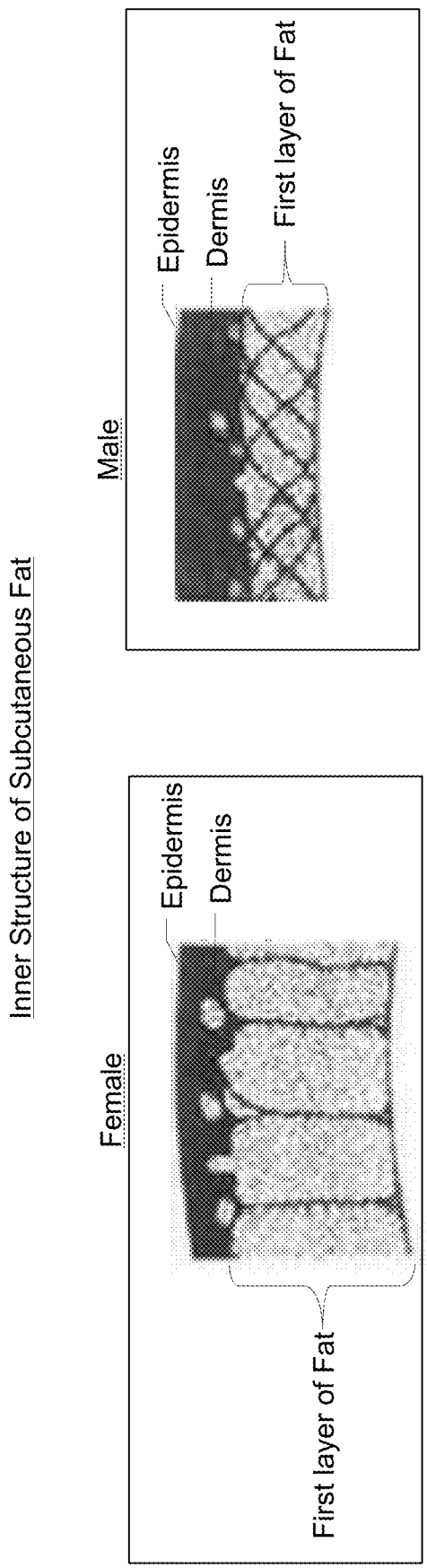
FIG. 1 is a side by side comparison of the inner structure of subcutaneous fat in both the female and male body, that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms.

Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Through extensive research testing and development, the inventors have discovered that cellulite and/or the appearance of cellulite deposits can be reduced through exposure to photonic energy that is applied by optical emitters at a target wavelength and for a specific duration of time. Moreover, the inventors have also discovered that actual fat deposits can be reduced because subcutaneous adipocytes will expel their lipid content when treated with the below described system and method.

In this regard, a cellulite and fat reducing device and method utilizing optical emitters can act to decrease the existence and/or appearance of cellulite deposits, and can also function to remove fat deposits without permanent or adverse effects on the cells and their surrounding tissues. The device can illuminate the epidermis, dermis and subcutaneous fat tissue by applying light/radiation from an array of optical emitters at a target wavelength. Such exposure functions to tighten and smooth the skin, and to reduce the size of subcutaneous fat in the exposed areas (typically the thighs and buttocks). Modulation is not required, but may enhance results.

As described herein, the term "optical emitter" can include any form of light producing and/or emitting device having any number of different colors across the color spectrum. Several non-limiting examples can include Light Emitting Diodes (LED's), light emitting capacitors, and/or super-luminous light emitting diodes, for example, that are capable of individually and/or jointly creating optical emissions of light/radiation at a target wavelength.

In the preferred embodiment, the below described array can utilize a plurality of green LED's. In this regard, studies have shown that exposure to green light induces a photochemical reaction within the human body that induces a biological cascade at the cellular level. This cascade promotes collagen synthesis at the location where the light is received and thus causes the skin at this location to tighten. Stated differently, the application of the green light causes structural corrections to the irregular pattern of the connective tissue associated with collagen. These effects result in an improvement in the appearance of cellulite, as measured by the Nurnberger-Muller Scale, thus reducing the appearance of the dimpling effects of cellulite. Additionally, exposure to the optical output of the array at the below described target wavelength can ultimately eliminate the underlying fat deposits causing the appearance of cellulite on the skin.

As described herein, a "target wavelength" and an "optical output" shall be used interchangeably to describe the measurable light/radiation output of one or more optical emitters, and/or the below described array that is sufficient to apply about 383 Lux subcutaneously to the cellulite fat deposits (i.e., target area) located on a human recipient for a total delivered energy of 8.8 Joules (typically requiring an exposure duration of between 15 and 25 minutes).

As human skin and the underlying tissue reflects and/or absorbs light, it is necessary that the measurable light/radiation output leaving the array be greater than the amount that is desired to make contact with the subcutaneous fat deposits of the recipient. In one embodiment, this measurable optical output (measurable at the array itself) shall include an output of green light at approximately 529.6 nm, at approximately 48,860 Lux. When the array is positioned at a distance of between 1 and 8 inches from the skin/target area of the recipient, approximately 383 Lux (of the 48,860 produced by the array) can penetrate the skin and can be delivered to the subcutaneous fat deposits. Of course, the distance and time can be slightly adjusted to account for the inherent variances of skin makeup from one person to another. In either instance, upon receiving the 383 Lux at 529.6 nm for approximately 15 to 25 minutes, the desired energy of 8.8 Joules will be delivered, thereby reducing the fat deposits which, along with the above described collagen production causes an immediate and noticeable reduction in the existence and/or appearance of cellulite at the target area.

As is known to those of skill in the art, unlike lasers, which are monochromatic and can be manufactured to produce an identifiable and constant wavelength, LEDs have a distribution of colors. Therefore, LEDs have a spectrum distribution as opposed to a fixed wavelength that takes into account light output and color. As such, current manufacturing techniques may be unable to provide a plurality of LEDs which can each deliver an exact peak or dominant wavelength at exactly 529.6 nm on a consistent basis. Therefore, when utilizing LEDs, within the below described array, the optical output can include an output spectrum approaching or as close to 529.6 nm as possible so as to deliver about 383 Lux subcutaneously. Such a feature can be accomplished by individually testing the output of each LED prior to positioning the light within the array.

Accordingly, when operating in the target wavelength i.e. at a suitable power dosimetry, e.g., from about 50 mW/cm2 to about 110 mW/cm2, the device can effectively reduce the existence and/or appearance of cellulite as described above.

Turning now to the drawings, where identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 2.

Figure 2:
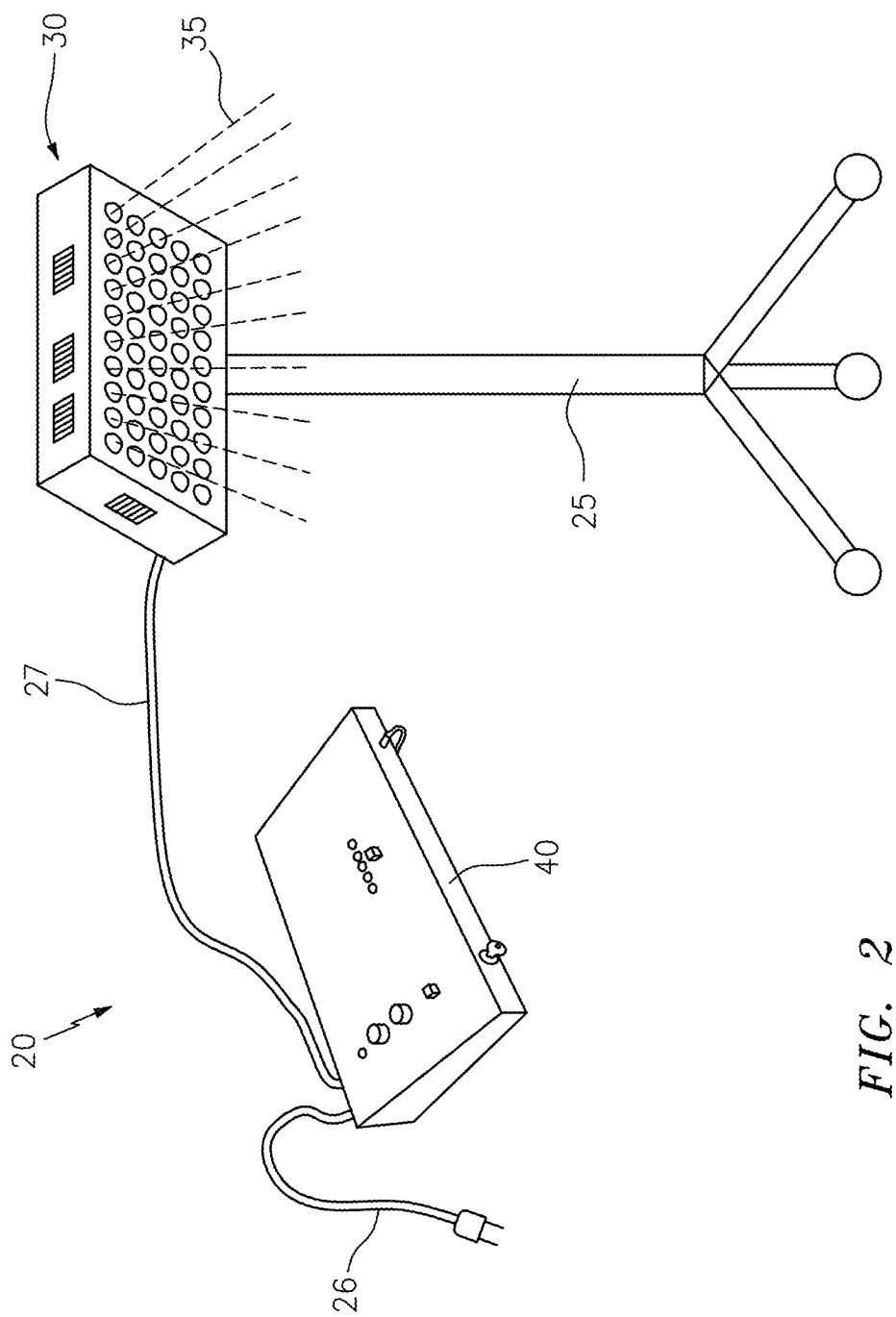
FIG. 2 is a perspective view of the cellulite and fat reducing device utilizing optical emitters in accordance with one embodiment of the invention.

FIG. 2 illustrates one embodiment of a cellulite and fat reducing device utilizing optical emitters that is useful for understanding the inventive concepts disclosed herein. As shown, the device 20 can include an array of optical emitters 30 (array) which can operate to produce photonic energy in the form of light/radiation 35 at a target wavelength when instructed by a controller 40. A multi-positional stand 25 can be secured to the array 30 for precise alignment and positioning over a recipient. The controller 40 can include a power cable 26 for mating with a conventional 120V AC power source, and a second cable 27 can be provided to supply power from the controller 40 to the array 30.

Figure 3A:
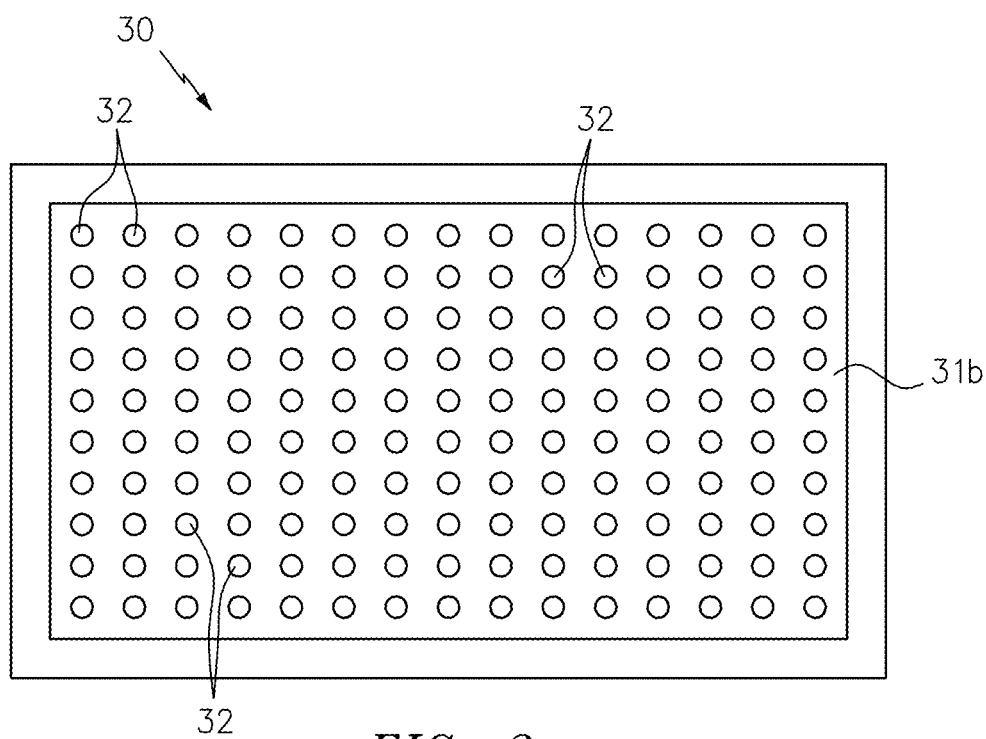
FIG. 3a is a bottom side view of the array for use with the cellulite and fat reducing device utilizing optical emitters in accordance with one embodiment of the invention.
Figure 3B:
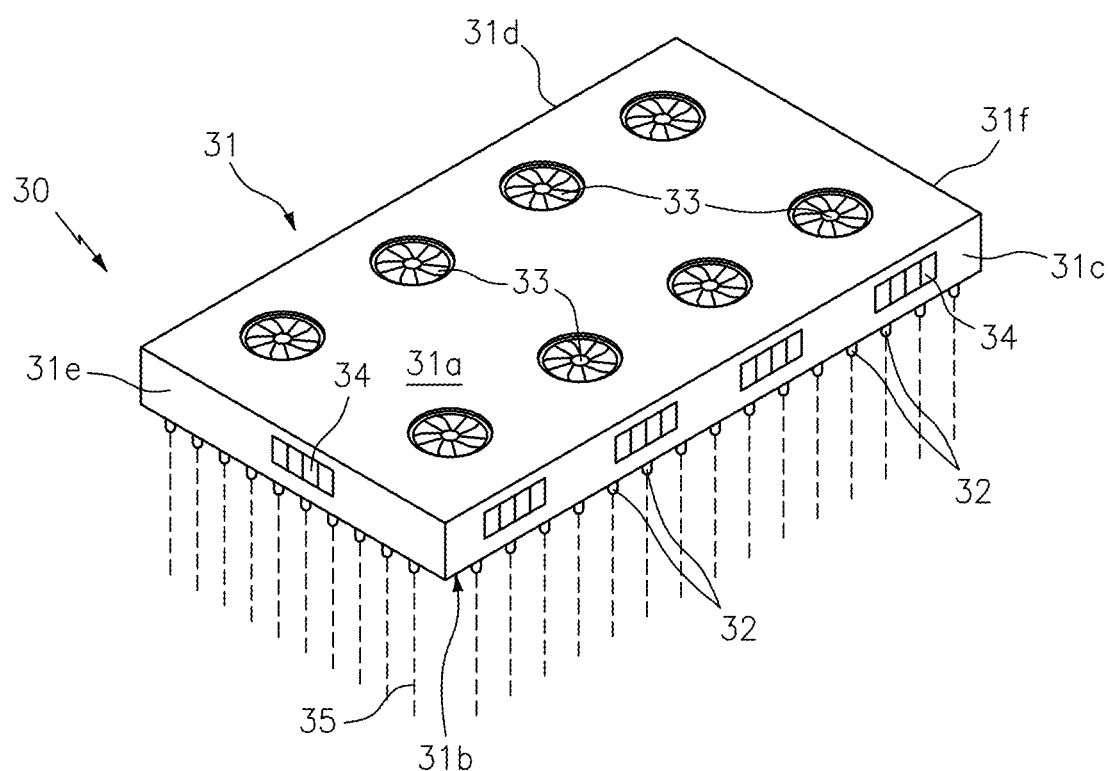
FIG. 3b is a perspective side view of the array of the cellulite and fat reducing device utilizing optical emitters in accordance with one embodiment of the invention.

FIGS. 3a and 3b illustrate one embodiment of a suitable array 30. The array can include a generally rectangular main body having a top surface 31a, a bottom surface 31b, a front surface 31c, a back surface 31d and opposing side surfaces 31e and 31f, each forming a generally hollow interior space. A plurality of optical emitters 32 are positioned within the main body 31 so as to allow the emissions therefrom to be directed outward from the bottom surface 31b. Additionally, a plurality of ventilation devices such as fans 33 heat syncs (not shown) and/or air vents 34 can be provided on or within the main body to allow proper air ventilation.

In one preferred embodiment, the main body can be constructed from metal, and the plurality of optical emitters 32 can include, comprise or consist of 150 2-Watt green LED's that operate at 120V AC power from the cable 27, at the discretion of the controller 40. When power is provided to the array 30, the plurality of emitters 32 can produce an optical output at the target wavelength. Owing to the shape and size of the body portions most commonly afflicted with the appearance of cellulite, the array can preferably include a dimension of approximately 20 inches by 20 inches, suitable for easily directing the optical emitters to the desired target area. Moreover, the shape of the array can be curved, so as to enable the optical emitters to reach around the curved surfaces of a recipient's buttocks, thighs and hips. Of course, the array is not limited to any particular shape, size and/or dimension.

Although described above as including a specific shape, size, construction material, type and number of light emitting sources, this is for illustrative purposes only, as those of skill in the art will recognize that many different combinations and types of optical emitters and/or main body shapes and construction materials can also be utilized to achieve the desired optical output described above. Moreover, although illustrated as protruding out from the main body, the optical emitters 32 can also be flush mounted in accordance with known manufacturing techniques.

Figure 4A:
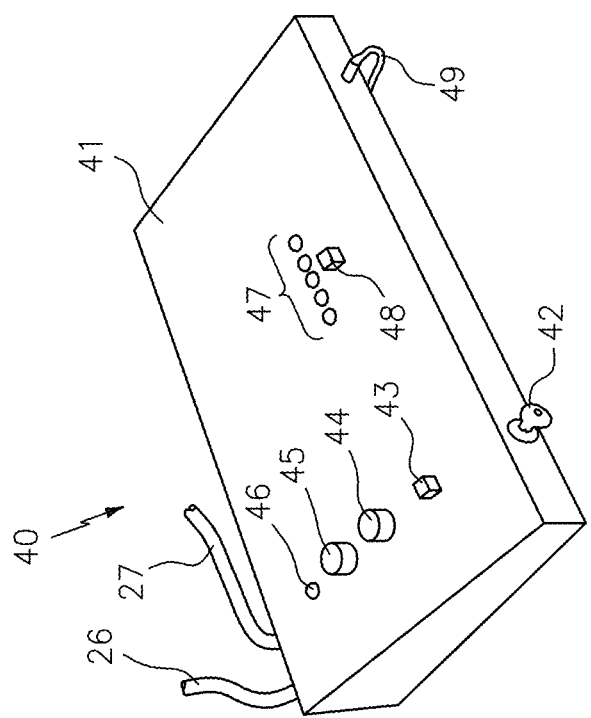
FIG. 4a is a perspective view of the controller of the cellulite and fat reducing device utilizing optical emitters in accordance with one embodiment of the invention.

FIG. 4a illustrates an exterior view of one embodiment of the controller 40. As shown, the controller can include a main body 41 having a plurality of user controls and/or interface devices secured thereon. These devices can include, for example, a key switch 42, a stop button 43, a volume selector 44, an exposure time selector 45 an array indicator 46, a modulation signal strength indicator (VU meter) 47, a start button 48 and a signal input jack 49. Of course any number of other interface devices can also be provided, as necessary or desired to control the functionality of the array.

Figure 5A:
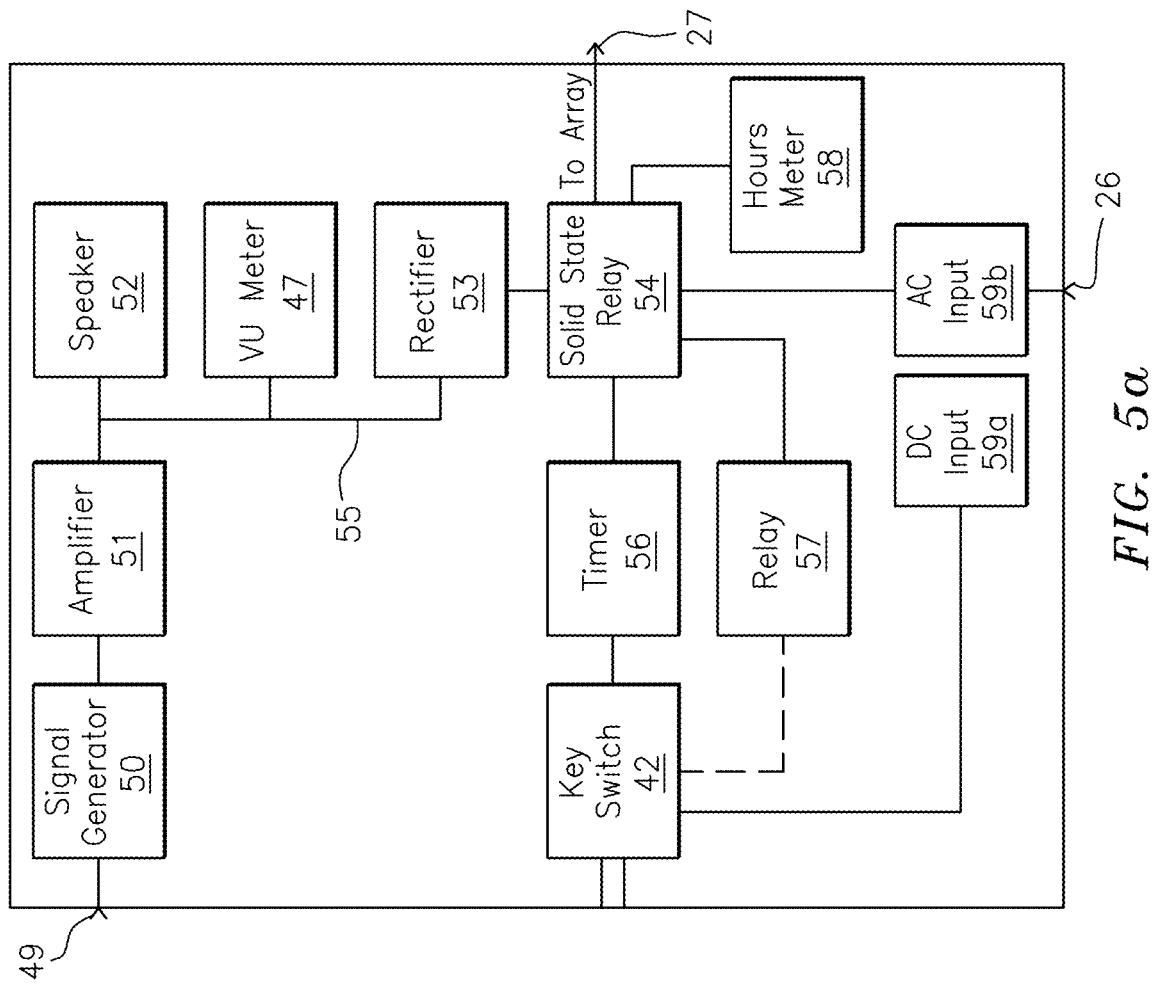
FIG. 5a is a schematic block circuit diagram of the controller of the cellulite and fat reducing device utilizing optical emitters in accordance with one embodiment of the invention.

FIG. 5a illustrates one embodiment of a circuitry block diagram of the controller 40 described above. As shown, the internal components can include, for example, a signal generator 50, an amplifier 51, one or more speakers 52, a rectifier 53, one or more solid state relays 54, a timer 56, a control switch relay 57, an hours meter 58, an AC power input device 59b, and a DC power module 59a. Each of these components and the user interfaces described above can be communicatively linked via one or more internal cables 55, bus or other suitable device. The above described diagram is exemplary in nature, as any number of different and/or additional components necessary for operation of the device are also contemplated.

Although described above as including specific features, those of skill in the art will recognize that any means for controlling the operation of the array can be provided herein. To this end, the controller 40 can be manufactured in accordance with any number of known construction methodologies, and one or more of the internal components, although listed as separate elements, can be formed together to form a printed circuit board or other such component, for example, in accordance with known manufacturing processes.

The main body 41 can act to securely position each of the elements 42-59 in secure manner so as to form a single unit which can be operated by a user. The body itself can take any number of distinct shapes and sizes, and can be constructed from any number of known materials such as plastic or metal, for example. Of course, other known materials and manufacturing processes are also contemplated.

The key switch 42 can function to provide security against operation of the device by unauthorized persons. To this end, the key switch can interface with a physical key and an internal relay 57 to switch the device between a plurality of operating states. For example, the key can switch the device between: on with internal modulation selected, device off, and device on with external modulation source selected. Although illustrated herein as using a physical key, other access control devices can also be utilized herein. Several non-limiting examples including: key fob, access code (via an integrated keypad), biometric sensors and the like.

The stop button 43 can function to immediately cease power distribution to the array 30 when engaged. The speaker volume selector 44 can comprise a switch or knob, for example, which acts to control the output of the one or more speakers 52. The exposure time selector 45 can comprise a switch or knob, for example, which can allow a user to specify how long power will be sent to the array during a particular treatment. The array indicator 46 can include a light or other such notification instrument suitable for notifying a user when power is being sent to the array.

The modulation signal strength indicator 47 can act to indicate the presence of an external modulation signal, and to display a visual representation of the signal to a user. The visual representation also indicating the delivery of power to the array 30. The start button 48 functions to initiate the device timer 56 and allows power to be sent to the array 30.

One or more input jacks 49 can be provided to allow the controller 40 to interface with an external device such as a computer/tablet device, radio, television, CD player, DVD player, or MP3 player, for example. These external devices can generate and transmit an audio or sub audio input signal i.e., reference waveform such as music or words, for example, to the controller 40. In one preferred embodiment, the input jack 49 can include a standard ⅛ inch modulation input jack (e.g., mini-phone plug) and/or other forms of input devices such as a USB port, for example.

The input jack 49 can be connected to the internal signal generator 50 such as an audio oscillator, for example, which can act to either generate or pass through the received reference waveform.

In operation, the controller 40 can be connected to a conventional 120V AC input source, which can supply power to the internal DC module 49 for powering the controller interfaces. The received AC power can also be modulated and subsequently transferred to the array 30 which can utilize the same to generate an optical output. The controller 40 and/or array 30 can also include any number of fuses to protect the recipient, operator and device in the event of an electrical problem or excessive current flow through the device components. The flow of electricity (120 VAC) to the array 30 can be controlled by the timer circuit 56, which can interface with the start button 48, stop button 43, the exposure time selector 45 and the array indicator 46.

Together with array positioning relative to the client's body, the controller 40 can vary the fluency of the photonic energy delivered to the skin and underlying tissue. The start button 48 begins the timer circuit 56, which allows power to be sent to the array 30 for conversion into light via the plurality of optical emitters 32. When the array is illuminated, the hours meter 58 advances to record the total operation time of the device.

The controller 40 can execute a method to control the fluency by modulation of the current transmitted to the optical emitters 32 of the array 30. In one embodiment, the current to the array 30 can vary based on the frequency of the reference waveform (i.e., audio input signal) that is internally generated 50 or that is generated by an external device and connected to the input jack 49.

The reference waveform 61 (see FIG. 6*a*) can be supplied to the amplifier 51 before being sent to the rectifier 53. The rectifier can function to produce an output voltage representing only the positive portion of the reference waveform. This output voltage 62 (See FIG. 6*b*) can function to activate the Solid-State Relay (SSR) 54, and the negative portion is shunted to ground. As such, when the SSR is active, 120V AC power can be passed to the array 30 for conversion into light via the plurality of optical emitters 32. Alternatively, when the output voltage 62 is not present, or drops below a predetermined threshold, the SSR can prevent the 120V AC power from passing to the array 30 until the next positive cycle of the reference signal 61. As such, modulation of the array output is accomplished by varying the current and pulse width of the 120V AC voltage supplied to the array 30 from the controller 40.

The VU Meter 47 can be in communication with the signal generator and rectifier in order to provide a visual indicator of the input frequency strength for purposes of adjustment. The audio amplifier 51 can also provide the input signal to the speaker 52 so as to allow the operator to simultaneously listen to the input signal. Each of the amplifier and speaker can be controlled by the volume selector 44 in order to vary the volume of the monitored input signal.

The content of the audio input signal controls the array fluency with respect to time, affecting and controlling the photonic energy delivered to the skin and underlying tissue. A different audio recording (or video recording with sound) will result in the array having a different fluency and excitation patterns with respect to time, which further results in varying photochemical and biochemical responses and outcomes at a cellular level. By providing a means for communicating with an external device, the controller 40 can allow an operator maximum flexibility for generating a virtually unlimited number of array fluencies through modulation of various audio input signals.

Although described above as including the ability to produce a modulated signal, other embodiments are also contemplated. To this end, the device 20 can be operated without modulation, wherein the controller 40 can provide a constant and steady power source to the array 30 for a specific period of time.

Figures 4B, 5B:
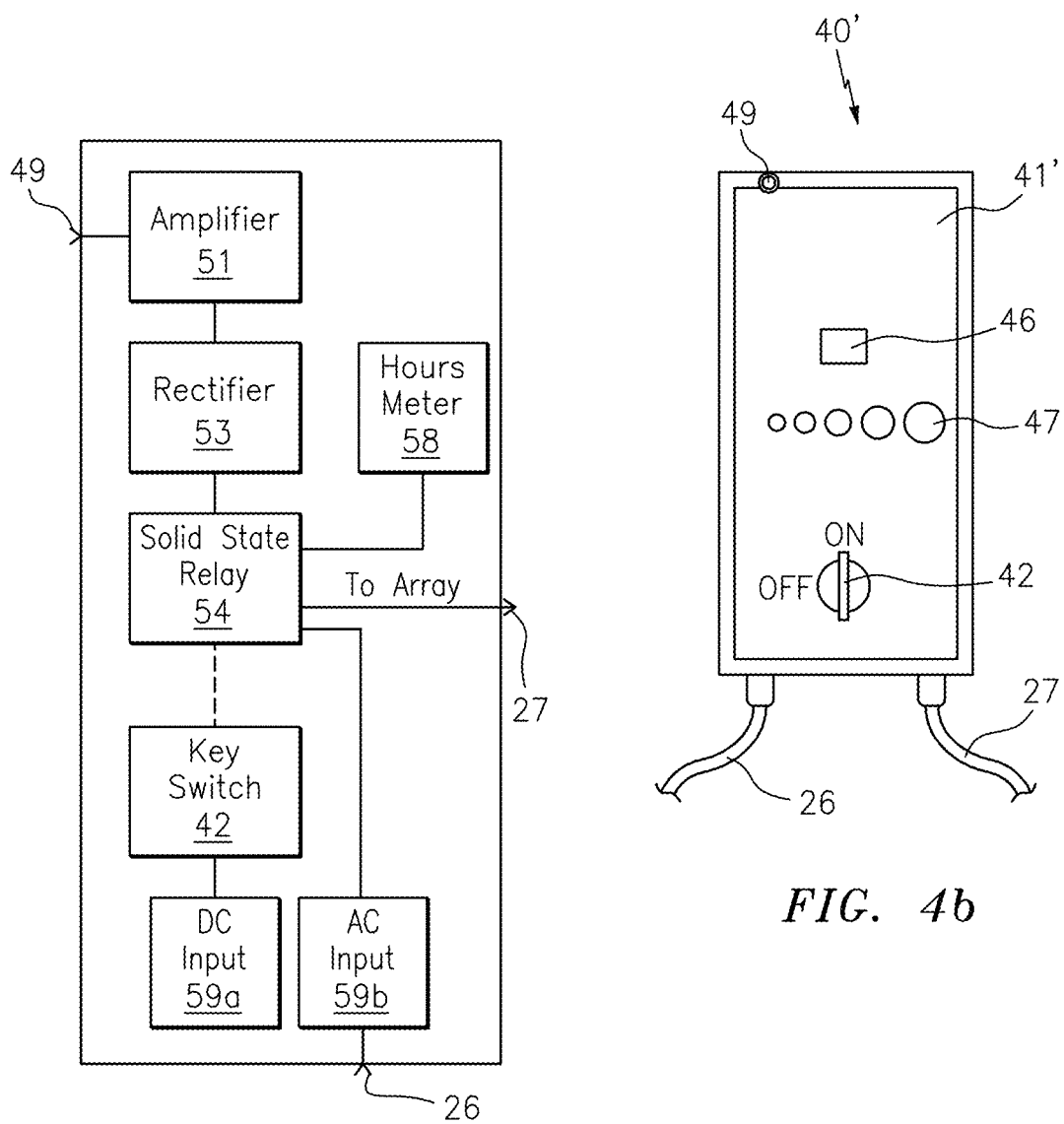
FIG. 4b is a perspective view of the controller of the cellulite and fat reducing device utilizing optical emitters in accordance with another embodiment of the invention.
FIG. 5b is a schematic block circuit diagram of the controller of the cellulite and fat reducing device utilizing optical emitters in accordance with another embodiment of the invention.

Although described above with respect to particular components, those of skill in the art will recognize that the inventive concepts disclosed herein can be accomplished by substituting certain components for other functionally equivalent components, or by reducing the number of components into a more simplified controller. To this end, FIGS. 4*b*, and 5*b*, illustrate another embodiment of a controller for operating the array 30.

As shown, controller 40' can also include a main body 41', having one or more user controls and/or interface devices secured thereon. These devices can also include a key switch 42, an array indicator 46, a modulation signal strength indicator 47, and a signal input jack 49. Of course any number of other interface devices can also be provided. As shown by the exemplary circuitry block diagram, the controller 40' can include, for example, an amplifier 51, a rectifier 53, one or more solid state relays 54, an hour meter 58, an AC power input 59*b* and a DC power module 59*a*.

In the present embodiment, the key switch 42 functions to replace the start button and the stop button. In this regard, when the key switch is in the on position, the controller 40' provides power to the array 30 based on a reference waveform received by the input jack 49, as described above. Conversely, when the key is in the off position, no power is sent to the array, and the DC power to the controller components is disabled. Such a feature can allow the size of the controller to be small in nature, typically between about 14 and 20 inches, so as to enable the device to be easily transported.

Figure 7:
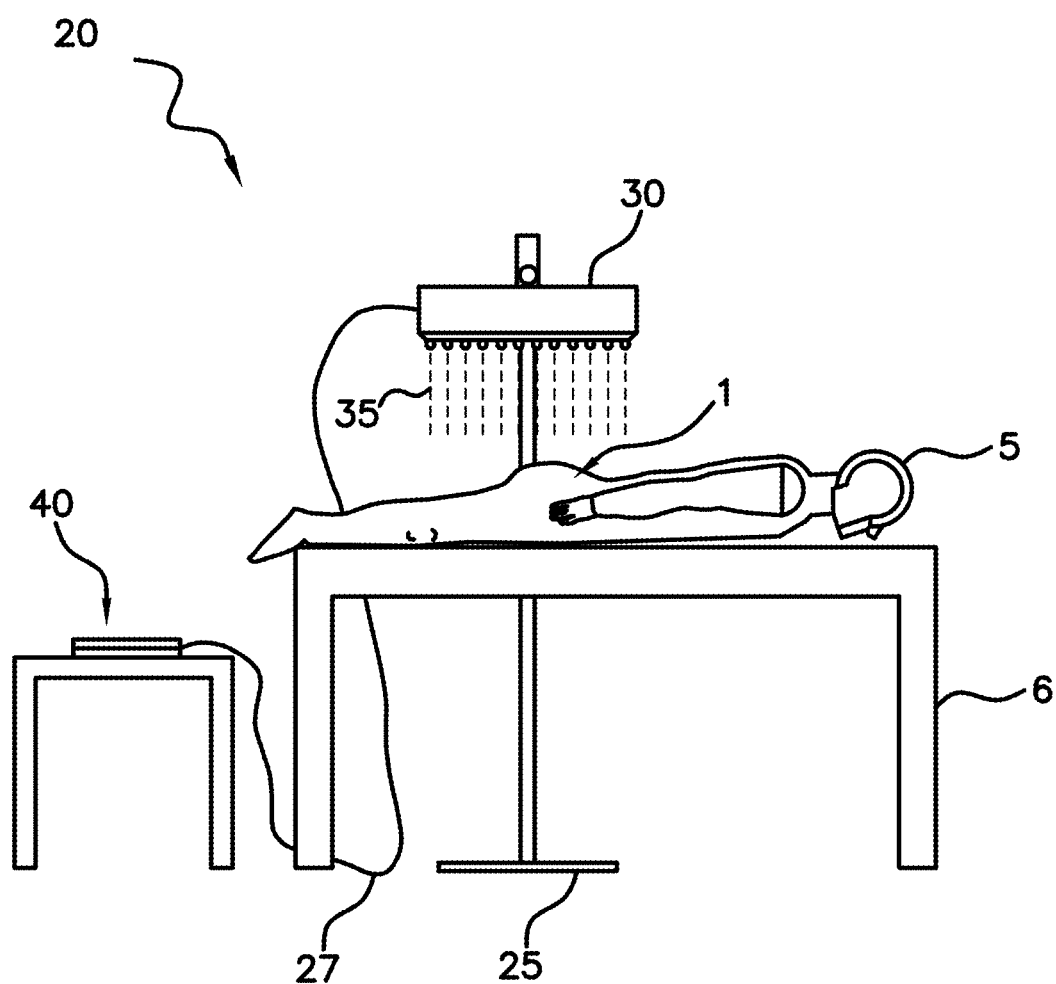
FIG. 7 is a perspective view of the cellulite and fat reducing device utilizing optical emitters in operation, and in accordance with one embodiment of the invention.

FIG. 7 illustrates one embodiment of the cellulite and fat reducing device utilizing an array of optical emitters 30 to treat a recipient. As shown, the recipient 5 can be positioned on a table 6 or other suitable platform, and the array 30 can be positioned above the target area 1 (in this example, the buttocks) of the recipient via the stand 25.

The array can be positioned at any desirable distance from the target area of the recipient and an operator (not shown) can utilize the controller 40 to activate the array. Once activated, the optical emitters of the array can produce the optical output 35 described above at the target wavelength, for any desirable period of time such as between 1 and 30 minutes, for example, although the preferable exposure time will be approximately 20 minutes.

Figure 8:
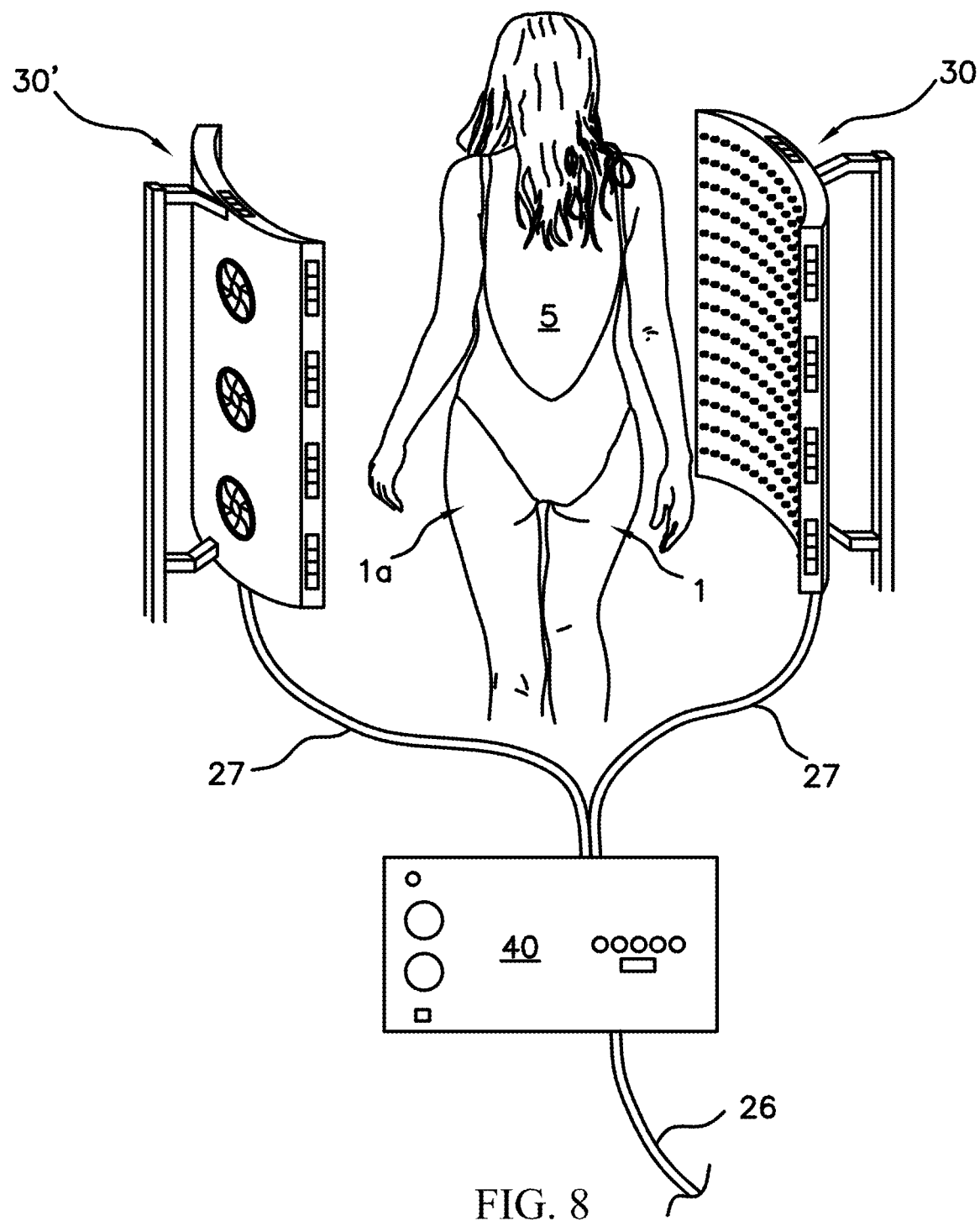
FIG. 8 is a perspective view of the cellulite and fat reducing device utilizing optical emitters in operation, and in accordance with an alternate embodiment of the invention.

Although described above with reference to a single controller and a single array, other embodiments are also contemplated. FIG. 8 illustrates another embodiment of the device 20 wherein a plurality of curved arrays 30 and 30' can operate in unison to treat symmetrical target areas 1 and 1*a* of a recipient 5 simultaneously. In this regard, the illustrated example shows treatment for the thighs of the recipient, but can easily be adjusted to treat the hips and the upper arms, for example.

As described herein array 30' can be constructed in an essentially identical manner as array 30 described above, and each of the arrays can be tethered 27 to a single controller 40. In this regard, a single device 20 can function to treat multiple areas of a recipient at one time.

Figure 9:
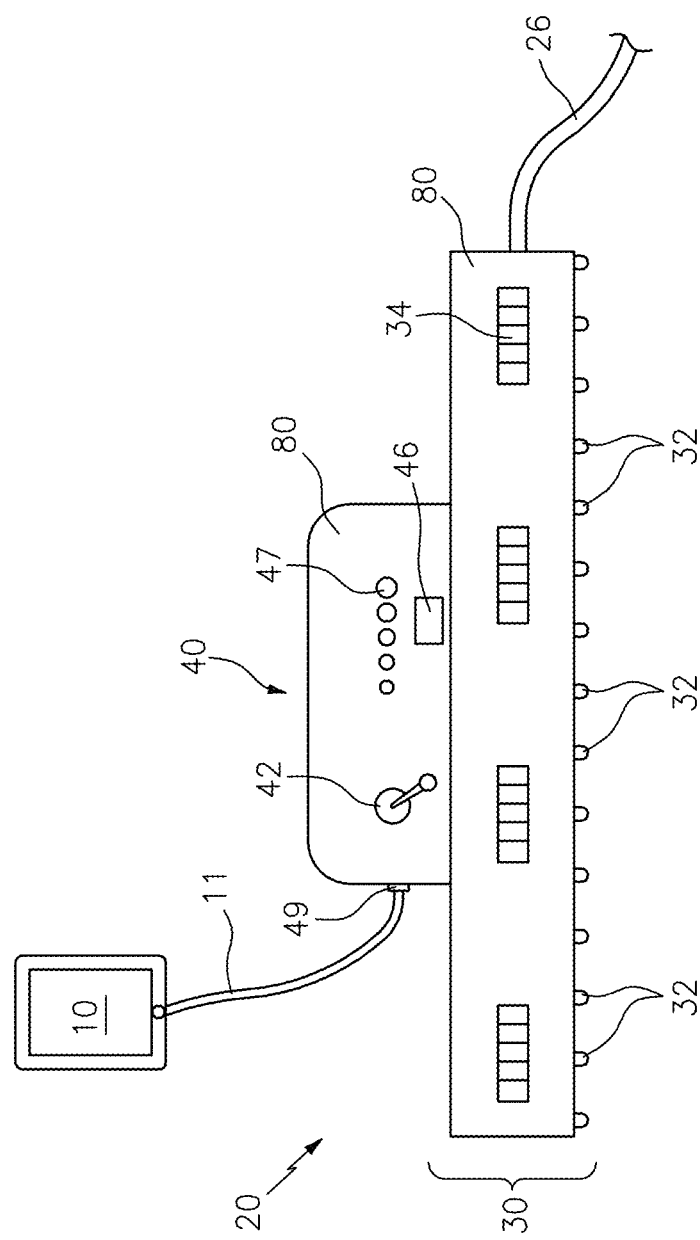
FIG. 9 is a perspective view of the cellulite and fat reducing device in accordance with another alternate embodiment of the invention.

FIG. 9 illustrates yet another embodiment of the device 20, wherein the controller 40 and array 30 are integrated into a singular structure. In the present embodiment, the controller main body 41 and the array main body 41 are joined to create a unified main body 90 that houses the controller and array components as heretofore described. As shown, the device 20 can be connected to an external device 10 (in this instance a tablet pc) via an audio cable 11 in order to receive the audio signal.

By providing a more simplified array and controller, as described above, the device can operate in a self-service capacity. To this end, the user interfaces of the controller can be accessible to a recipient at all times during treatment. Such a feature can allow the recipient/end user to control the physical operation of the device at all times, thereby ensuring compliance with any jurisdictional laws or regulations regarding the operation of such equipment by anyone other than the end user/recipient. In this regard, the device will preferably be equipped with only the on/off switch, however any number of other user interfaces can also be provided.

As described herein, one or more elements of the controllers 40 and 40' and the arrays 30 and 30' can each be constructed utilizing any number of known means of attachment such as, for example, screws, glue, compression fittings and welds, among others. Moreover, although various components may be described herein as including separate individual elements, other embodiments are contemplated wherein multiple individual components are formed together as one continuous element, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for reducing the appearance of cellulite and fat on a recipient's body, said method comprising:
    providing an output array having a plurality of optical emitters, and a controller for instructing an operation of the array;
    generating a reference waveform by the controller;
    generating an output voltage based only on a positive portion of the reference waveform;
    identifying a target area of a recipient;
    positioning the plurality of optical emitters toward the target area of the recipient;
    producing, via the array, an optical output at a target wavelength, said optical output comprising green light at 529.6 nm, and at 48,860 Lux;
    delivering, via the plurality of optical emitters, optical emissions totaling 8.8 Joules of energy to the target area of the recipient to reduce an appearance of visible cellulite and to expel a lipid content of the subcutaneous adipocytes, said optical emissions comprising green light at 383 Lux at the wavelength of 529.6 nm for a time of between 15 and 25 minutes;
    modulating the optical output based on the output voltage;
    wherein each of the plurality of optical emitters comprise, at least one of, a light emitting capacitor, a light emitting diode, and a super-luminous light emitting diode.

2. The method of claim 1, wherein the plurality of optical emitters consists of:
    150 2-Watt green Light Emitting Diodes (LEDs), each individually tested to produce an output spectrum of approximately 529.6 nm.

3. A method for reducing the appearance of cellulite and fat on a recipient's body, said method comprising:
    providing an output array having a plurality of optical emitters, and a controller for instructing an operation of the array;
    identifying a target area of a recipient;
    positioning the plurality of optical emitters toward the target area of the recipient;
    producing, via the array, an optical output at a target wavelength, said optical output comprising green light at 529.6 nm, and at 48,860 Lux;
    delivering, via the plurality of optical emitters, optical emissions totaling 8.8 Joules of energy to the target area of the recipient to reduce an appearance of visible cellulite and to expel a lipid content of the subcutaneous adipocytes, said optical emissions comprising green light at 383 Lux at the wavelength of 529.6 nm for a time of between 15 and 25 minutes;
    wherein each of the plurality of optical emitters comprise, at least one of, a light emitting capacitor, a light emitting diode, and a super-luminous light emitting diode;
    wherein the target area includes a dimension of about 12 inches by 12 inches measurable on the recipient.

4. The method of claim 3, further comprising:
    generating a reference waveform by the controller, and modulating the optical output based on the reference waveform.

5. The method of claim 4, further comprising:
    generating an output voltage based only on a portion of the reference waveform; and
    modulating the optical output based on the output voltage.

6. The method of claim 4, wherein the portion of the reference waveform is a positive portion of the reference waveform.

7. The method of claim 3, further comprising:
    receiving a reference waveform from an external device; and
    modulating the optical output based on the received reference waveform.

8. The method of claim 3, wherein the plurality of optical emitters consists of:
    150 2-Watt green Light Emitting Diodes (LEDs), each individually tested to produce an output spectrum of approximately 529.6 nm.

* * * * *